US006762600B2

(12) United States Patent
Khalfin

(10) Patent No.: US 6,762,600 B2
(45) Date of Patent: Jul. 13, 2004

(54) METHOD AND APPARATUS FOR ELECTROMAGNETIC POSITION AND ORIENTATION TRACKING WITH DISTORTION COMPENSATION EMPLOYING A MODULATED SIGNAL

(75) Inventor: Igor Khalfin, Pleasanton, CA (US)

(73) Assignee: Polhemus, Inc., Colchester, VT (US)

( * ) Notice: Subject to any disclaimer, the term of this patent is extended or adjusted under 35 U.S.C. 154(b) by 0 days.

(21) Appl. No.: 10/699,949

(22) Filed: Nov. 3, 2003

(65) Prior Publication Data

US 2004/0090226 A1 May 13, 2004

Related U.S. Application Data

(63) Continuation of application No. 10/428,540, filed on May 2, 2003, now abandoned, and a continuation of application No. 10/164,081, filed on Jun. 4, 2002, now Pat. No. 6,624,626, which is a continuation-in-part of application No. 09/430,978, filed on Nov. 1, 1999, now Pat. No. 6,400,139.
(60) Provisional application No. 60/377,918, filed on May 2, 2002.

(51) Int. Cl.$^7$ ............................................. G01B 7/14
(52) U.S. Cl. ................. 324/207.17; 324/252; 324/248; 324/253; 324/247; 600/407; 600/424; 702/150
(58) Field of Search ......................... 324/207.2–207.26; 702/150; 600/407, 424; 342/448, 463

(56) References Cited

U.S. PATENT DOCUMENTS

| | | | |
|---|---|---|---|
| 4,314,251 A | 2/1982 | Raab | ........................... 343/112 |
| 4,737,794 A | 4/1988 | Jones | ........................... 342/448 |
| 5,453,686 A | 9/1995 | Anderson | ..................... 324/207 |
| 5,645,077 A | 7/1997 | Foxlin | ........................... 128/774 |
| 5,752,513 A | 5/1998 | Acker et al. | ................. 128/653 |
| 5,754,049 A | 5/1998 | Howell | ........................... 324/326 |
| 5,831,260 A | 11/1998 | Hansen | ......................... 250/221 |
| 6,369,564 B1 | 4/2002 | Khalfin et al. | .......... 324/207.17 |
| 6,377,041 B1 | 4/2002 | Jones, Jr. et al. | ............ 324/244 |
| 6,400,139 B1 * | 6/2002 | Khalfin et al. | .......... 324/207.17 |
| 6,529,006 B1 | 3/2003 | Hayes | ........................... 324/326 |
| 6,539,327 B1 | 3/2003 | Dossot et al. | ................ 702/150 |

FOREIGN PATENT DOCUMENTS

EP          0 747 662 A1    6/1996

* cited by examiner

Primary Examiner—Jay Patidar
(74) Attorney, Agent, or Firm—Gifford, Krass, Groh, Sprinkle, Anderson & Citkowski, PC

(57) ABSTRACT

A bounding box or volume of interest is flooded with a modulated AC electromagnetic signal from a source. Different types of modulated signals may be used, including single-tone AM and FM. One or more sensors disposed on an object or body within the volume are then used to detect the signal, and a digital and/or analog spectral and phase analysis is performed on the received signal in hardware or software. The processing distinguishes between the direct source to sensor response and the response due to eddy currents. By removing the response due to the distorters, the effects of the electromagnetic distortion can be removed through a more conventional "free-space" solution. The invention finds applicability in a wide variety of environments, including head tracking systems and helmet-mounted displays for fighter aircraft; head trackers for armored vehicles; medical-guided surgery and biopsy; remote sensing, among other potential uses.

35 Claims, 1 Drawing Sheet

METHOD AND APPARATUS FOR ELECTROMAGNETIC POSITION AND ORIENTATION TRACKING WITH DISTORTION COMPENSATION EMPLOYING A MODULATED SIGNAL

REFERENCE TO RELATED APPLICATIONS

This application is a continuation of U.S. patent application Ser. No. 10/428,540, filed May 2, 2003 now abandoned, which claims priority from U.S. Provisional Patent Application Serial No. 60/377,918, filed May 2, 2002 and is a continuation of U.S. patent application Ser. No. 10/164,081, filed Jun. 4, 2002, now U.S. Pat. No. 6,624,626, which is a continuation-in-part of U.S. patent application Ser. No. 09/430,978, filed Nov. 1, 1999, now U.S. Pat. No. 6,400,139. The entire content of each application is incorporated herein by reference.

FIELD OF THE INVENTION

This invention relates generally to position/orientation tracking and, in particular, to methods and apparatus for accurately tracking position, orientation and movement within a volume in the presence of electromagnetic distortion and/or noise.

BACKGROUND OF THE INVENTION

Position and orientation tracking systems ("trackers") are well known in the art. For example, U.S. Pat. Nos. 4,287,809 and 4,394,831 to Egli et al.; U.S. Pat. No. 4,737,794 to Jones; U.S. Pat. No. 4,314,251 to Raab; and U.S. Pat. No. 5,453,686 to Anderson, are directed to AC electromagnetic trackers. U.S. Pat. No. 5,645,077 to Foxlin discloses an inertial system, and combination systems, consisting or two different trackers, such as optical and magnetic, are described in U.S. Pat. No. 5,831,260 to Hansen and U.S. Pat. No. 6,288,785 B1 to Frantz et al. Other pertinent references include U.S. Pat. No. 5,752,513 to Acker et al. and U.S. Pat. No. 5,640,170 to Anderson.

AC electromagnetic trackers have definite advantages over other types of systems. For one, AC trackers provide the highest solution/update rate with the greatest accuracy, not affected by obstructed field of view, in contrast to optical solutions. AC trackers do not require reference sensor/unit and drift stable apparatus of the type required by inertial units, and they are not affected by the Earth's magnetic field and ferrous materials, in contrast to DC magnetic systems.

The main disadvantage of AC trackers is that they are quite susceptible to distortion due to eddy currents in conductive materials in or near the motion box. To overcome this phenomenon, magnetic trackers often require costly and time-consuming calibration/mapping procedures to function correctly in the distorted environment. With mapping, the magnetic field profile is measured at multiple points associated with the volume of interest (motion box) prior to the actual tracking, as discussed in commonly assigned U.S. Pat. No. 6,377,041 to Jones et al., and some of the references cited therein. While mapping may be done quickly and accurately, any changes in the motion box will require repeating of the mapping procedure.

Another approach, described in U.S. Pat. No. 6,147,480 to Osadchy et al., allows the AC tracker to trace moving metal (distortion) by measuring the signal without distortion (acquiring baseline signals). This signal is then compared with a signal in the presence of distorting object(s) by measuring the phase error of the received signal. While such a system does work, it is not always practical to acquire baseline signal without distortion; in many cases, in an aircraft cockpit, for example, the distortion is always present.

The approach described in U.S. Pat. No. 6,172,499 B1 to Westley introduces at least two frequencies per source channel, and uses the difference in responses to compensate for the eddy current distortion. This approach requires a guess about the eddy currents loop geometry, and the efficiency of the distortion compensation and operational frequencies depends on assumptions regarding the distorted environment, including the physical characteristics of the distorting materials where the system will be working. In addition, this approach requires a comparatively wide-band receiver (sensor and ADC processing), thus reducing noise stability.

The methods and apparatus for distortion compensated AC tracking described in our commonly assigned U.S. Pat. Nos. 6,400,139 and 6,369,564, both to Khalfin et al., take advantage of wired "witness" sensors to obtain real-time information concerning the distortion (this is done by analyzing field profile that is superposition of the source field and distortion fields at the locations of "witness" sensors given sufficient "witness" sensors data). In addition, the '564 patent describes the signal processing from a resonantly tuned wireless passive sensor, 90° phase shifted with respect to the source to enable separation of the distortion signal.

Despite these advances, the need remains for apparatus and methods of compensation for spurious, eddy-current-induced fields in AC electromagnetic tracking systems. Such a solution could take advantage of the fact that the electromagnetic coupling which creates these eddy currents is strongly dependent on the frequency of the transmitted AC magnetic field. In addition, eddy currents are phase shifted with respect to the magnetic tracker source drive current that generates the magnetic field.

SUMMARY OF THE INVENTION

According to the system and method described herein, a bounding box or volume of interest is flooded with a modulated AC electromagnetic signal from a source. Different types of modulated signals may be used, including single-tone AM and FM. One or more sensors disposed on an object or body within the volume are then used to detect the signal, and a digital and/or analog spectral and phase analysis is performed on the received signal in hardware or software. The processing distinguishes between the direct source to sensor response and the response due to eddy currents. After removing the response due to the distorters, the electromagnetic position/orientation problem can be treated through a conventional "free-space" solution.

The disclosed system and methods do not require witness sensors, though the approach may be used in a combination with them. The invention operates in a narrow frequency band to ensure noise stability, and preferably uses high operating frequencies (e.g., of about 20 kHz–50 kHz) to ensure high signal quality and increased operation range.

A rapid solution update rate may be used to achieve real time (per frame) distortion compensation without any prior knowledge about physical properties of the distorters. At the same time, the system preserves all known advantages of AC trackers, but without the need for a calibration/mapping procedure, which has proven to be the main obstacle to more widespread applications of AC electromagnetic tracking technology.

The invention finds applicability in a wide variety of environments, including head tracking systems and helmet-mounted displays for fighter aircraft; head trackers for armored vehicles; medical-guided surgery and biopsy; remote sensing, among other potential uses.

DETAILED DESCRIPTION OF THE INVENTION

Figure 1:
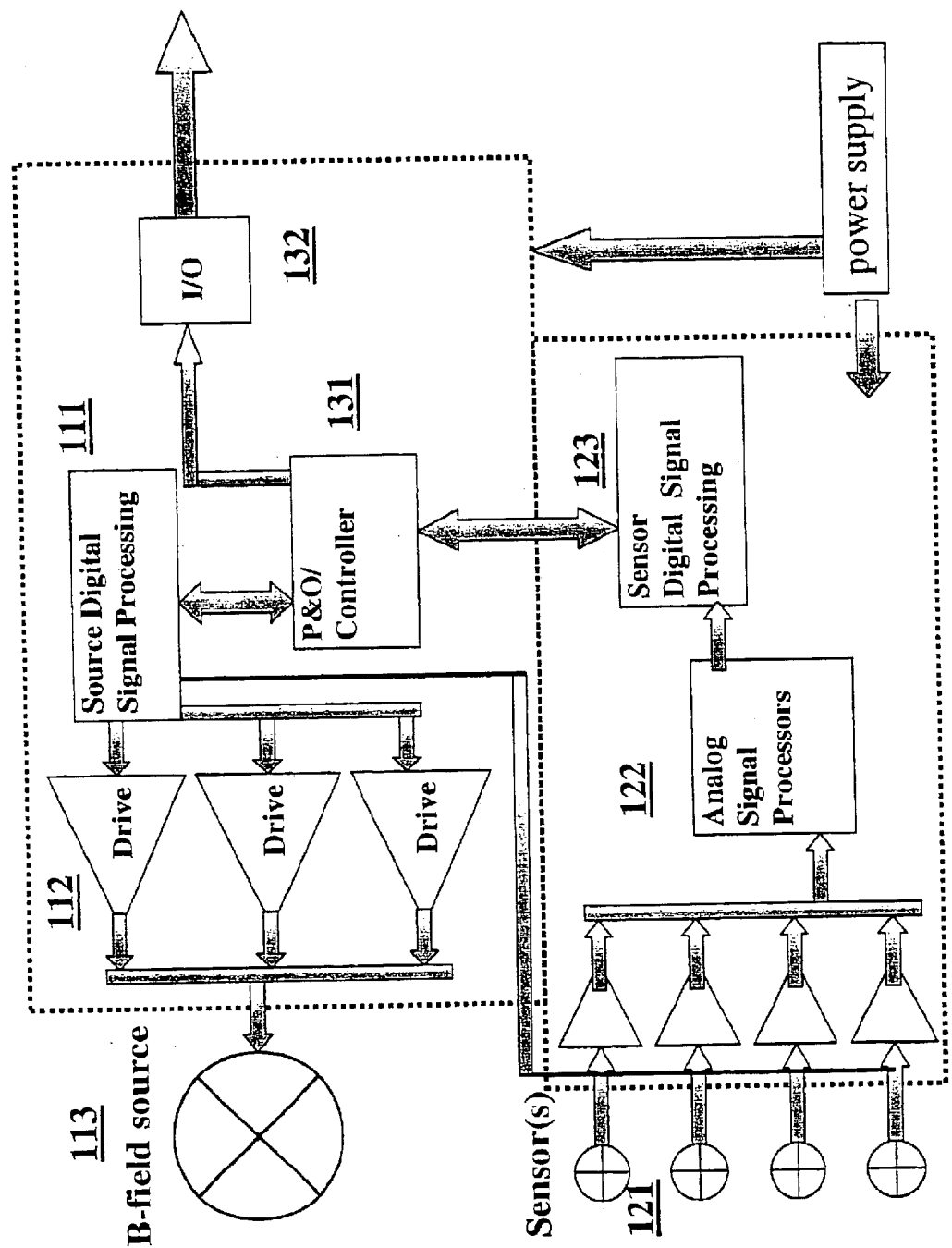
FIG. 1 is a block diagram of a preferred embodiment of the invention.

According to the invention, a source processor generates a modulated waveform, for example, a single-tone FM or single-tone AM signal, preferably having a modulation frequency close to the carrier frequency (for example, 30 kHz carrier and 20 kHz modulation). In the preferred embodiment, the waveform is detected by a sensor containing several non-coplanar coils, and a demodulation and spectral analysis is performed on the received signal.

The symmetry pattern of the carrier/satellites allows the system to distinguish between source-sensor coupling and source-distorter-sensor coupling, since each coupling modality is frequency-dependent and has unique phase characteristics. The restored source-sensor response then is plugged into a "free-space" solution which is well known in the art.

Thus, in contrast to prior-art systems, the inventive approach monitors and stabilizes the phase and the magnitude of the source (transmitter) current with respect to the internal reference. Without such stabilization, source drive current may change due to the electromagnetic coupling between the source and conducting materials in the volume of interest, as well as because of drift in electronics hardware.

A functional diagram of a system according to the preferred embodiment of the invention is presented in FIG. 1. A source processor 111 generates the signal components representative of the modulated waveform. The modulated signal feeds source drivers 112 and is transmitted by a B-field source 113.

The modulated signal is received by a sensor or sensors 121, and the induction-vector components are demodulated and analyzed by analog and/or digital signal processors 122 and 123. At this stage, the signal is cleansed from the effects of the electromagnetic distortion. The resulting data is then transmitted to the "free-space" position and orientation processor 131, and the result is output to a utilization device via I/O controller 132.

It should be noted that the system with additional sensors working as "witnesses" might be arranged thus providing additional distortion and error correction. The use of witness sensors is disclosed in U.S. Pat. No. 6,400,139 to Khalfin et al., the entire content of which is incorporated herein by reference.

The number of coils per sensor and per source may vary, depending on the number of DOF (degrees of freedom) to be measured. It is preferred to have three non-parallel sensor coils and three non-parallel source coils for six degrees of freedom. In addition to search coils, the sensors may use any appropriate magnetic flux sensing device including, but not limited to, solid-state (GMR or PSS), quantum (SQID), or flux gage sensors.

EXAMPLE

The method of distortion compensation in the case of single-tone FM modulation will now be described with the understanding that various alternative modulation schemes may be used.

The waveform generated by the source drive may be given as:

$$\cos(2\pi f_c t - \alpha \sin(2\pi f_m t)) \quad (1)$$

This signal has well-pronounced components at $f_c - f_m, f_c$, and $f_c + f_m$, $f_c > f_m$.

The sensor(s) receive a signal that is time derivative of the source signal multiplied by a coupling constant that contains all sufficient information about position and orientation of the sensor with respect to the source. In a non-distorted environment, the data is sampled at 90 degrees behind the source, i.e., —sin DFT (discrete Fourier transform) and, after the DFT, the satellite and carrier components are:

$$\frac{\alpha}{2} b = S1 \quad (2a)$$

$$b = S2 \quad (2b)$$

$$-\frac{\alpha}{2} b = S3, \quad (2c)$$

where S1, S2, and S3 are sensor responses normalized to the frequencies, b corresponds to the matrix element of the coupling matrix: $\|b\| = \mu\mu_o$, Att $A_{eff}$ D M. All further considerations have as their goal the restoration of S2 in a distorted/scattering environment.

In the presence of distortion, an additional term quadratic with respect to the frequency (linear, after normalization) appears with magnitude a and with the phase shift of the carrier frequency $\phi$, given that in this case the data are sampled at the zero phase of the non-distorted response. In general, the satellites exhibit different phase shifts from the carrier which are proportional to the deviation of frequencies. Note, no information or estimates about the values of $\phi$ and $\alpha$ are necessary for further computations.

For the Im part of the acquired signal, e.g., 90 degrees behind the non-distorted source phase, we have:

$$-\frac{\alpha}{2} a 2\pi (f_c - f_m) \sin(\varphi - \Delta\varphi) + \frac{\alpha}{2} b = SD1 \quad (3a)$$

$$-a 2\pi (f_c) \sin(\varphi) + b = SD2 \quad (3b)$$

$$\frac{\alpha}{2} a 2\pi (f_c + f_m) \sin(\varphi + \Delta\varphi) - \frac{\alpha}{2} b = SD3 \quad (3c)$$

For the Re part we have:

$$-\frac{\alpha}{2} a 2\pi (f_c - f_m) \cos(\varphi - \Delta\varphi) = CD1 \quad (4a)$$

$$-a 2\pi (f_c) \cos(\varphi) = CD2 \quad (4b)$$

$$\frac{\alpha}{2} a 2\pi (f_c + f_m) \cos(\varphi + \Delta\varphi) = CD3 \quad (4c)$$

Combining terms in equations (3) and (4), and using symmetry of the satellites with respect to the carrier, we arrive at:

$$(SD1 + SD3)^2 + (CD1 - CD3)^2 - \alpha^2 CD2^2 = \alpha^2 (SD2 - S2)^2 f_m^2 / f_c^2 \quad (5)$$

Taking into account practical consideration that the distortion contribution to the signal is not greater than the direct response and removing the ambiguity of sign we obtain the result:

$$S2 = \quad (6)$$
$$b = sign(SD2)\left[-\frac{1}{\alpha}\frac{f_c}{f_m}\sqrt{(SD1+SD3)^2 + (CD1-CD3)^2 - \alpha^2 CD^2} + sign(SD2)SD2\right]$$

Equation (6) defines a restored, "non-distorted" signal in the presence of distortion.

The values of b from different sensor coils (3 for 6DOF) are sufficient to find position and attitude matrix as it was noted after equation (2).

I claim:

1. A method of determining the position and orientation of an object or body within a bounded volume containing an AC electromagnetic field distorter, comprising the steps of:
   modulating an AC magnetic field carrier frequency with a modulation waveform to generate a source signal having induction-vector components corresponding to the carrier and modulation (satellites);
   stabilizing magnitude and phase of the modulated source signal with respect to the internal reference
   providing a sensor to measure the induction-vector components at the location of the object or body;
   analyzing the induction-vector components of the carrier and satellites to distinguish between source-sensor coupling and source-distorter-sensor coupling; and
   using the source-sensor coupling to compute the position and orientation of the sensor, and hence, the object or body.

2. The method of claim 1, wherein the AC magnetic field carrier is amplitude modulated.

3. The method of claim 1, wherein the AC magnetic field carrier is frequency modulated.

4. The method of claim 1, wherein the AC magnetic field carrier is amplitude or frequency modulated with a single tone.

5. The method of claim 1, wherein the frequency of the modulation is somehow lower than the carrier.

6. The method of claim 1, wherein the steps (generation and measurements) are performed within narrow frequency bands.

7. The method of claim 1, wherein the symmetry between carrier and satellites is known.

8. The method of claim 1, further including the steps of:
   positioning at least one stationary witness sensor near or within the volume of interest;
   measuring the induction-vector components at the witness sensor using a known fixed position and orientation; and
   using the induction-vector components from each witness sensor to more accurately compute the position and orientation.

9. The method of claim 1, wherein the signal received by the sensor is a time derivative of the source signal multiplied by a coupling constant.

10. The method of claim 1, wherein the object or body includes a person's head or other body part.

11. The method of claim 1, wherein the object or body includes a medical instrument.

12. The method of claim 1, wherein the object or body is associated with remote sensing.

13. The method of claim 1, wherein the steps are performed in real time or near real time.

14. The method of claim 1, wherein the sensor operates along two or more independent axes to detect multiple degrees of freedom.

15. The method of claim 1, wherein the sensor is a magnetic-field search coil.

16. The method of claim 15, wherein the three non-parallel sensor search coils and three non-parallel source coils for six degrees of freedom.

17. The method of claim 1, wherein the sensor is a solid-state (GMR or PSS), quantum (SQID), or flux gage magnetic flux sensor.

18. A system for determining the position and orientation of an object or body within a bounded volume containing an AC electromagnetic field distorter, comprising:
   a source of a modulated AC magnetic field having induction-vector components;
   an electronic circuit stabilizing magnitude and phase of the modulated source signal with respect to the internal reference;
   a sensor to measure the induction-vector components at the location of the object or body; and
   one or more processors to perform the following functions:
      analyze the induction-vector components of the carrier and satellites to distinguish between source-sensor coupling and source-distorter-sensor coupling, and
      compute the position and orientation of the sensor, and hence, the object or body based on the source-sensor coupling.

19. The system of claim 18, wherein the AC magnetic field is amplitude modulated.

20. The system of claim 18, wherein the AC magnetic field is frequency modulated.

21. The system of claim 18, wherein the AC magnetic field carrier is amplitude or frequency modulated with a single tone.

22. The system of claim 18, wherein the frequency of the modulation is somehow lower than the carrier.

23. The system of claim 18, wherein the AC magnetic field components are generated and measured within narrow frequency bands.

24. The system of claim 18, wherein the symmetry between carrier and satellite frequencies is known.

25. The system of claim 18, wherein the sensor operates along two or more independent axes to detect multiple degrees of freedom.

26. The system of claim 18, further including a stationary witness sensor positioned near or within the volume of interest to measure the induction-vector components using a known fixed position and orientation.

27. The system of claim 18, wherein the signal received by the sensor is a time derivative of the source signal multiplied by a coupling constant.

28. The system of claim 18, wherein the object or body includes a person's head or other body part.

29. The system of claim 18, wherein the object or body includes a medical instrument.

30. The system of claim 18, wherein the steps are performed in real time or near real time.

31. The system of claim 18, wherein the sensor operates along two or more independent axes to detect multiple degrees of freedom.

32. The system of claim 18, wherein the sensor is a magnetic-field search coil.

33. The system of claim 18, wherein the three non-parallel sensor search coils and three non-parallel source coils for six degrees of freedom.

34. The system of claim 18, wherein the sensor is a solid-state (GMR or PSS), quantum (SQID), or flux gage magnetic flux sensor.

35. In a tracking system of the type wherein source of an AC electromagnetic field having induction-vector components is received by a sensor on an object or body within a bounded volume to determining the position and orientation of the object or body in the presence of a field distorter, the improvement comprising:

modulating the AC electromagnetic field;

stabilizing magnitude and phase of the modulated source field components analyzing the induction-vector components corresponding to the carrier and modulation frequencies and detected by the sensor to distinguish between source-sensor coupling and source-distorter-sensor coupling; and computing the position and orientation of the sensor, and hence, the object or body based on the source-sensor coupling.

* * * * *